United States Patent [19]
Richter et al.

[11] 3,951,922

[45] Apr. 20, 1976

[54] PROCESS FOR PREPARING POLYIMIDES FROM DERIVATIVES OF PHTHALIC ANHYDRIDE

[75] Inventors: Reinhard H. Richter, Hamden; Henri Ulrich, North Branford, both of Conn.

[73] Assignee: The Upjohn Company, Kalamazoo, Mich.

[22] Filed: June 10, 1974

[21] Appl. No.: 477,629

Related U.S. Application Data

[62] Division of Ser. No. 228,376, Feb. 22, 1972, Pat. No. 3,829,444.

[52] U.S. Cl. .......................... 260/78 A; 260/47 CP; 260/77.5 R; 260/78 TF; 528/84; 528/288
[51] Int. Cl.² ........................................ C08G 75/10
[58] Field of Search ........ 260/78 A, 77.5 R, 78.4 R, 260/78 TF, 47 CB, 47 CP

[56] References Cited
UNITED STATES PATENTS
3,109,836    11/1963    Berry ................................... 260/78

*Primary Examiner*—Lester L. Lee
*Attorney, Agent, or Firm*—Denis A. Firth; John Kekich

[57] ABSTRACT

The compounds 4-azidocarbonylphthalic anhydride, 4-isocyanatophthalic anhydride, and the lower-alkyl carbamates obtained by reacting the latter isocyanate with a lower-aliphatic alcohol, are described. A process for the preparation of a polyimide by heating these compounds alone or in admixture with other polyisocyanates is also described. The 4-azidocarbonylphthalic anhydride is an intermediate for the 4-isocyanatophthalic anhydride.

3 Claims, No Drawings

PROCESS FOR PREPARING POLYIMIDES FROM DERIVATIVES OF PHTHALIC ANHYDRIDE

This is a division of application Ser. No. 228,376 filed Feb. 22, 1972, and now U.S. Pat. No. 3,829,444.

BACKGROUND OF THE INVENTION

1. Field of the Invention

This invention relates to isocyanates and intermediates therefor and is more particularly concerned with isocyanatophthalic anhydride, intermediates therefor, and derivatives and polymers produced therefrom.

2. Description of the Prior Art

The 4-azidocarbonyl- and 4-isocyanatophthalic anhydrides, and the lower-alkyl carbamates of the latter, described herein are believed to be novel and applicants are not aware of any pertinent prior art.

Polyimides, closely related to those which are prepared as described hereinafter, are disclosed in U.S. Pat. No. 3,503,928 as being prepared by self-polymerization of 4-aminophthalic anhydride.

SUMMARY OF THE INVENTION

The invention comprises compounds of the formula:

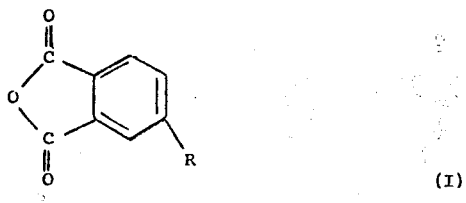

(I)

wherein R is selected from the class consisting of $-CON_3$, isocyanato and $-NHCOOR'$ wherein R' is lower-alkyl. The invention also comprises a process for the preparation of polyimides by (a) self-polymerization of the compounds of the formula (I) by heating the latter or (b) copolymerization of the compounds of formula (I) with an organic polyisocyanate.

DETAILED DESCRIPTION OF THE INVENTION

The compound of formula (I) wherein R = azidocarbonyl is prepared readily by reaction of 4-chlorocarbonylphthalic anhydride (1,2-anhydrotrimellitic acid chloride; see R. G. Barker et al., J. Chem. Soc. 1964, 3475; C.A. 61, 13230) with sodium azide under conditions well known in the art for the preparation of carboxylic acid azides; see, for example, Powell, J. Amer. Chem. Soc. 1929, 51, 2436.

The 4-azidocarbonylphthalic anhydride so obtained is then converted to the corresponding isocyanate (I; R = NCO) using the Curtius rearrangement which involves heating the azide in the presence of an inert solvent such as toluene until evolution of gas ceases; see, for example, the procedure described by Curtius, J. prakt. Chem. [2] 50, 275, 1894. If desired, the isocyanate can be prepared directly from the corresponding chlorocarbonylphthalic anhydride without isolation of the intermediate azide in accordance with the procedure known as the Curtius reaction also described in the above reference paper of Curtius.

The lower-alkyl carbamates (I; R = $-NHCOOR'$) of the invention are prepared by reaction of the 4-isocyanatophthalic anhydride with a substantially equimolar proportion of a lower aliphatic alcohol such as methanol, ethanol, propanol, butanol, pentanol, hexanol and the like. The term "lower-alkyl" means alkyl from 1 to 6 carbon atoms, inclusive, such as methyl, ethyl, propyl, butyl, pentyl, hexyl, and isomeric forms thereof.

The reaction between the isocyanate and the lower aliphatic alcohol takes place readily upon simply admixing the two reactants, usually in the presence of an inert organic solvent such as benzene, toluene, xylene and the like. The reaction is exothermic in nature but external heat can be applied if it is desired to increase the reaction rate particularly in the case of the higher aliphatic alcohols.

The compounds of the formula (I) all possess the property of forming a highly useful polyimide by self-condensation upon exposure to heat. The process is illustrated schematically in the following equation which represents the self-condensation of the 4-isocyanatophthalic anhydride.

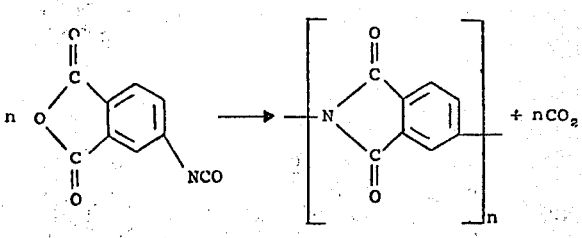

In the case of the self-condensation of the 4-azidocarbonylphthalic anhydride, the first step is presumably the Curtius rearrangement of the azide to the corresponding isocyanate followed by self-condensation of the latter in accordance with the above equation. In the case of the lower-alkyl carbamates, the first step is presumably regeneration of the isocyanate with elimination of lower-aliphatic alcohol followed by self-condensation of the isocyanate as above.

The polyimides obtained as described above are solid materials which can be fabricated in the form of high temperature resistant articles by appropriate molding operations. The molding is accomplished generally by converting the polyimide to a fine powder and subjecting the latter to molding using techniques conventionally employed in molding powdered metals such as by sintering or hot pressing; see, for example, "Encyclopedia of Chemical Technology", edited by Kirk and Othmer, Interscience Encyclopedia Inc., Vol. 11, pages 54–55, New York, 1953. In this manner the polyimides produced in accordance with this invention can be molded in the form of bushings, seal faces, electric insulators, compressor vanes and impellers, pistons and piston rings, gears, thread guides, cams, brake linings, clutch faces, abrasive articles and the like.

Copolyimides can also be derived from the compounds of formula (I) by polymerizing said compounds in the presence of one or more other organic polyisocyanates and a polycarboxylic polyanhydride. Examples of appropriate organic polyisocyanates and polycarboxylic polyanhydrides are those set forth in U.S. Pat. No. 3,620,987. Such copolymerization involves self-condensation of the compound (I) as well as interaction of the anhydride group of the compound (I) with isocyanate groups of the added polyisocyanate and interaction of the isocyanate group of the compound (I) with anhydride groups of the added anhydride. Some of the various possible reactions involved in the copolymerization are shown schematically by the following simplified equations:

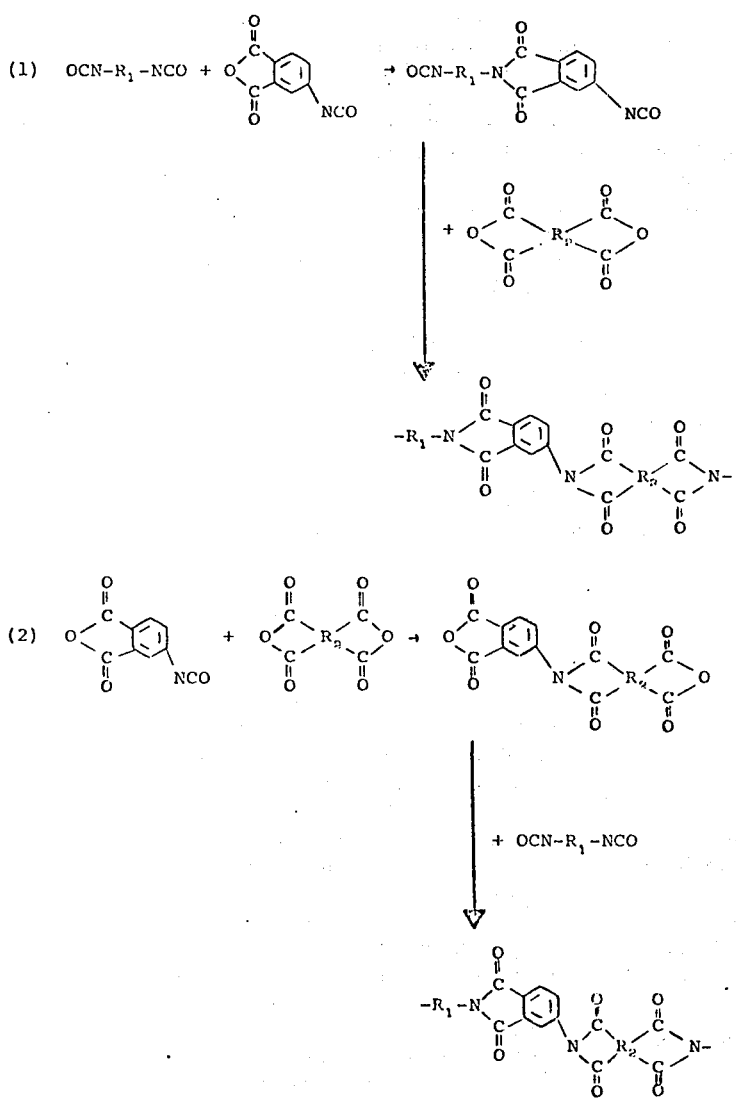

In the above equations $R_1$ represents the residue of the organic polyisocyanate (in the case shown, the polyisocyanate is a diisocyanate) and $R_2$ is the residue of a dianhydride. It is to be understood that the above equations are not intended to be an exhaustive representation of the various reactions which take place in the formation of the copolyimides but are given merely to facilitate an understanding of the manner in which the copolyimides are prepared. The proportion of the compound (1) which is employed in the formation of the copolyimides can be as low as about 1 mole for each 10 moles of added organic polyisocyanate and as high as 10 moles per mole of added organic polyisocyanate. The proportion of polycarboxylic polyanhydride which is present in the reaction mixture required to produce the copolyimide depends upon the relative proportions of compound (I) and added organic polyisocyanate. The amount of polycarboxylic polyanhydride used is such that the total molar proportion of anhydride groups present in the initial reaction mixture will be substantially equal to the total molar proportion of isocyanate groups present. In carrying out the copolymerization, the compound (I), the organic polyisocyanate, and the polycarboxylic polyanhydride are brought together and heated at a temperature in the range of about 250°C to about 300°C until evolution of carbon dioxide gas is complete. The copolyimide is formed as a solid residue.

The copolyimides so obtained are useful and can be molded and used in the manner and for all the purposes for which the polyimides obtained by self-condensation are molded and used as enumerated above.

The following examples describe the manner and process of making and using the invention and set forth the best mode contemplated by the inventors of carrying out the invention but are not to be construed as limiting.

EXAMPLE 1

A total of 3.25 g of sodium azide was added in portions to a solution of 10.5 g of 4-chlorocarbonylphthalic anhydride in 100 ml of acetone. The mixture was allowed to stand for 17 hours at room temperature (circa 25°C) after which the yellow solution so obtained was evaporated to dryness under reduced pressure. There was thus obtained a substantially quantitative yield of 4-azidocarbonylphthalic anhydride in the form of a crystalline solid having a melting point of 100° to 103°C with decomposition.

Anal: Calcd. for $C_9H_3N_3O_4$: C, 49.79; H, 1.39; N, 19.35; Found: C, 49.57; H, 1.32; N, 19.40

EXAMPLE 2

A solution of 10 g of 4-azidocarbonylphthalic anhydride (prepared as described in Example 1) in 100 ml of toluene was heated on a water bath at 95°C until evolution of gas substantially ceased (about 3 hours). At the end of this time the solution was filtered and the filtrate was evaporated to dryness. The residue was 9 g of 4-isocyanatophthalic anhydride in the form of a creamy white solid having a melting point of 65° to 72°C.

The product obtained in a second run using the above procedure was purified by sublimation to give colorless crystals of 4-isocyanatophthalic anhydride having a melting point of 80° to 82°C.

Anal: Calcd. for $C_9H_3NO_4$: C, 57.16; H, 1.60; N, 7.40; Found: C, 57.16; H, 1.49; N, 7.28.

EXAMPLE 3

A solution of 3.80 g (0.02 mole) of 4-isocyanatophthalic anhydride in 20 ml of benzene was treated dropwise, with stirring, with a solution of 0.64 g (0.02 mole) of methanol in 8 ml of benzene. An exothermic reaction occurred and the temperature of the mixture rose to 40°C. The resulting mixture was stirred overnight at room temperature (circa 25°C) and the solid which had separated was isolated by filtration, washed with a small amount of benzene and dried in vacuo. There was thus obtained 3.2 g of 4-methoxycarbonamidophthalic anhydride in the form of a crystalline solid having a melting point of 150° to 154°C.

Anal: Calcd. for $C_{10}H_7NO_5$: C, 54.30; H, 3.19; N, 6.33; Found: C, 53.97; H, 3.07; N, 6.03

Similarly, using the above procedure but replacing methanol by an equivalent amount of ethanol, butyl alcohol, or hexyl alcohol, there are obtained 4-ethoxy-, 4-butoxy-, and 4-hexyloxyphthalic anhydrides.

EXAMPLE 4

This example illustrates the preparation of a polyimide. A total of 4 g of 4-methoxycarbonamidophthalic anhydride (prepared as described in Example 3) was placed in a small flask which was immersed in an oil bath preheated to 180°C. The temperature of the bath was then raised to 250°C at which point the starting material had melted and evolution of gas had begun. The temperature of the oil bath was gradually raised to 300°C and maintained thereat until gas evolution from the melt ceased. The light colored solid residue was ground up, washed with acetone and ether and dried at 100°C. There was obtained 2 g of a polyimide which showed no signs of melting at temperatures up to 500°C.

The above procedure was repeated using 4-isocyanatophthalic anhydride and 4-azidocarbonylphthalic anhydride in place of the 4-methoxycarbonamidophthalic anhydride starting material and a polyimide was obtained in both cases.

We claim:

1. A process for the preparation of a solid polyimide which does not melt at temperatures below about 500°C and which has the recurring unit:

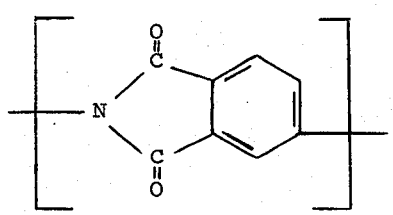

which comprises heating an anhydro compound having the formula:

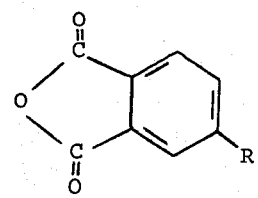

wherein R is selected from the class consisting of azidocarbonyl, isocyanato and —NHCOOR' wherein R' is lower-alkyl, at a temperature in the range of about 250°C to about 300°C until evolution of gas ceases.

2. A process in which the anhydro compound of claim 1 is heated at about 250° to about 300°C in the presence of an organic polyisocyanate and a polycarboxylic polyanhydride until evolution of gas ceases to form a solid copolyimide the organic polyisocyanate being employed in a proportion of from 0.1 mole to 10 moles per mole of said anhydro compound and the polycarboxylic polyanhydride being employed in a proportion such that the total number of anhydride groups present in the initial reaction mixture is substantially equal to the total number of isocyanate groups in said organic polyisocyanate plus the number of R groups in said anhydro compound.

3. A process according to claim 1 wherein the starting anhydro compound is 4-methoxycarbonamidophthalic anhydride.

* * * * *